United States Patent
Riley et al.

(10) Patent No.: US 9,024,104 B2
(45) Date of Patent: May 5, 2015

(54) METHODS FOR REMOVING WEAKLY BASIC NITROGEN COMPOUNDS FROM A HYDROCARBON STREAM USING BASIC MOLECULAR SIEVES

(71) Applicant: UOP LLC, Des Plaines, IL (US)

(72) Inventors: Mark G. Riley, Hinsdale, IL (US); Wugeng Liang, Elgin, IL (US); Deng-Yang Jan, Elk Grove Village, IL (US); Adam Gross, Glencoe, IL (US)

(73) Assignee: UOP LLC, Des Plaines, IL (US)

( * ) Notice: Subject to any disclaimer, the term of this patent is extended or adjusted under 35 U.S.C. 154(b) by 131 days.

(21) Appl. No.: 13/917,697

(22) Filed: Jun. 14, 2013

(65) Prior Publication Data

US 2013/0338417 A1    Dec. 19, 2013

Related U.S. Application Data

(60) Provisional application No. 61/661,369, filed on Jun. 19, 2012.

(51) Int. Cl.
| | |
|---|---|
| *C07C 7/12* | (2006.01) |
| *C07C 2/66* | (2006.01) |
| *C07C 7/13* | (2006.01) |

(52) U.S. Cl.
CPC ........................ *C07C 7/13* (2013.01)

(58) Field of Classification Search
USPC .................... 585/448, 820, 823, 824
See application file for complete search history.

(56) References Cited

U.S. PATENT DOCUMENTS

| | | | |
|---|---|---|---|
| 2,438,421 A | 3/1948 | Sensel | |
| 3,755,153 A | 8/1973 | Rosback | |
| 3,761,533 A | 9/1973 | Otani | |
| 5,220,099 A | 6/1993 | Schreiner | |
| 6,106,702 A | 8/2000 | Sohn | |
| 6,225,518 B1 | 5/2001 | Sohn | |
| 6,315,816 B1 | 11/2001 | Cho | |
| 6,423,881 B1 | 7/2002 | Yang | |
| 6,500,996 B1 | 12/2002 | Brown | |
| 6,894,201 B1 * | 5/2005 | Schmidt et al. | 585/448 |
| 7,205,448 B2 | 4/2007 | Gajda | |
| 8,546,630 B2 | 10/2013 | Jan | |
| 8,546,631 B2 | 10/2013 | Jan | |
| 8,546,632 B2 | 10/2013 | Jan | |
| 2006/0270886 A1 | 11/2006 | Brown | |
| 2009/0326291 A1 | 12/2009 | Jan | |
| 2013/0323133 A1 | 12/2013 | Liang | |
| 2013/0323134 A1 | 12/2013 | Riley | |
| 2013/0324773 A1 | 12/2013 | Liang | |
| 2013/0324774 A1 | 12/2013 | Riley | |
| 2013/0338416 A1 | 12/2013 | Riley | |

FOREIGN PATENT DOCUMENTS

EP    2186784 A2    5/2010

* cited by examiner

*Primary Examiner* — Thuan D Dang

(57) ABSTRACT

Disclosed is a method for removing weakly basic nitrogen compounds from a hydrocarbon feed stream by contacting the hydrocarbon feed stream with a basic catalyst to convert a portion of the weakly basic nitrogen compounds to basic nitrogen compounds. The method also includes contacting the hydrocarbon feed stream with an acidic adsorbent to adsorb the basic nitrogen compounds from the stream. The hydrocarbon feed stream comprises an aromatic compound and a weakly basic nitrogen compound.

13 Claims, No Drawings

METHODS FOR REMOVING WEAKLY BASIC NITROGEN COMPOUNDS FROM A HYDROCARBON STREAM USING BASIC MOLECULAR SIEVES

CROSS REFERENCE TO RELATED APPLICATION

This application claims the benefit of U.S. Provisional Application No. 61/661,369 which was filed on Jun. 19, 2012.

FIELD OF THE INVENTION

This invention relates to methods for removing nitrogen compounds from a hydrocarbon stream. More particularly, this invention relates to removing weakly basic nitrogen compounds from a hydrocarbon stream comprising aromatics.

BACKGROUND OF THE INVENTION

The use of molecular sieves as catalysts in aromatic conversion processes are well known in the chemical processing and refining industry. Aromatic conversion reactions of considerable commercial importance include the alkylation of aromatic compounds such as in the production of ethyltoluene, xylene, ethylbenzene, cumene, or higher alkyl aromatics and in disproportionation reactions such as toluene disproportionation, xylene isomerization, or the transalkylation of polyalkylbenzenes to monoalkylbenzenes. Often the feedstock to such an aromatic conversion process will include an aromatic component, i.e. alkylation substrate, such as benzene, and a C2 to C20 olefin alkylating agent or a polyalkyl aromatic hydrocarbon transalkylating agent. As used herein, terms such as "C4", "C5", "C6", etc. designate the number of carbon atoms per molecule of a hydrocarbon or hydrocarbon specie. In the alkylation zone, the aromatic feed stream and the olefinic feed stream may be reacted over an alkylation catalyst to produce alkylated aromatics, e.g. cumene or ethylbenzene. A portion or all of the alkylation substrate may be provided by other process units including the separation section of a styrene process unit. Polyalkylated benzenes are separated from monoalkylated benzene product and recycled to a transalkylation zone and contacted with benzene over a transalkylation catalyst to yield monoalkylated benzenes and benzene.

Catalysts for aromatic conversion processes generally include zeolitic molecular sieves. Examples include, zeolite beta (U.S. Pat. No. 4,891,458); zeolite Y, zeolite omega and zeolite beta (U.S. Pat. No. 5,030,786); X, Y, L, B, ZSM-5 and Omega crystal types (U.S. Pat. No. 4,185,040); X, Y, ultrastable Y, L, Omega, and mordenite zeolites (U.S. Pat. No. 4,774,377); and UZM-8 zeolites (U.S. Pat. No. 6,756,030 and U.S. Pat. No. 7,091,390). It is known in the art that the aromatic feed stream to aromatic conversion processes often contains nitrogen compounds, including weakly basic organic nitrogen compounds such as nitriles that can, even at ppm and ppb levels, cumulatively act to poison the downstream aromatic conversion catalysts such as aromatic alkylation catalysts and significantly shorten their life. A variety of guard beds having clay, zeolite, or resin adsorbents to remove one or more types of basic nitrogen compounds from an aromatic hydrocarbon stream upstream of an aromatic conversion process are known in the art. Examples include: U.S. Pat. No. 7,205,448; U.S. Pat. No. 7,744,828; U.S. Pat. No. 6,297,417; U.S. Pat. No. 5,220,099; WO 00/35836; WO 01/07383; U.S. Pat. No. 4,846,962; U.S. Pat. No. 6,019,887; and U.S. Pat. No. 6,107,535.

Water is often found in the aromatic feedstock to alkylation and transalkylation reactions, especially in benzene feed. Benzene feed is often water saturated, for example, when it is recycled from a styrene monomer unit. Molecular sieve catalysts employed in alkylation reactions in the vapor or the liquid phase may be sensitive to water at various levels or sulfur compounds in the feedstock. U.S. Pat. No. 4,107,224 discloses that water and hydrogen sulfide in vapor phase reactions may be tolerable if more rapid aging of the catalyst is acceptable. U.S. Pat. No. 5,030,786 disclose the dehydration of the feedstock to a water content of no more than 100 ppm, and preferably 50 ppm or less when the reaction zone is operated to maintain the reactor contents in the liquid phase. However, WO 93/00992 discloses that in the starting phase the zeolite catalyst for alkylation or transalkylation processes should have a minimum water content of more than 3.5 wt-%, related to catalyst composition. EP 0 922 020 B1 discloses uses of a solid acid to adsorb impurities from a benzene alkylation feed which is dried to contain no more than 200 ppm water at a temperature of between 130° and 300° C. to improve the lifetime of a zeolitic alkylation or transalkylation catalyst.

Other impurities present in the feedstock to an aromatic conversion reactor, particularly basic impurities such as basic organic nitrogen compounds (ONCs), neutralize the solid acids that comprise most present day aromatic alkylation catalysts. Catalyst performance and the catalyst life are adversely affected. Even very low nitrogen concentrations in the feed increase the catalyst regeneration frequency during which accumulated nitrogen compounds and coke must be combusted from the catalyst. As more active zeolite catalysts are employed in aromatic conversion reactions, the degradation of catalyst life by nitrogen impurities in the feedstock must be more carefully controlled. Processes are sought to reduce the impact of nitrogen impurities on the catalyst in the reaction zone. Basic nitrogen compounds that degrade catalyst life include indoles, pyridines, quinolines, diethanol amine (DEA), morpholines including N-formyl-morpholine (NFM) and N-methyl-pyrrolidone (NMP). NFM and NMP are used as aromatic extraction agents and DEA is a corrosion inhibitor that all often contaminate aromatic feed streams. Sacrificial guard beds have been used upstream of hydrocarbon conversion catalysts in order to remove the basic nitrogen compounds to protect the hydrocarbon conversion catalyst. For instance, U.S. Pat. No. 5,220,099 teaches removing indole, quinoline and pyridine impurities with zeolites and using toluene with dissolved water to desorb the impurities from the zeolites. WO 00/35836 discloses contacting an alkylated benzene with molecular sieve to remove catalyst poisons including nitrogen compounds prior to feeding it to a transalkylation reactor. WO 01/07383 discloses contacting a feed stream to an alkylation zone with a zeolite to remove organically bound nitrogen. U.S. Pat. No. 4,846,962 discloses contacting a solvent extracted oil with an amorphous silica-alumina or crystalline zeolite adsorbent to remove basic nitrogen compounds such as NMP. The adsorbent may contain up to 30 wt-% water.

U.S. Pat. No. 5,271,835 discloses the presence of polar impurities in the C3 to C5 product fraction from a fluid catalytic cracking unit. The impurities were found to include weakly basic ONCs such as acetonitrile. Acrylonitriles and propionitrile can also be found in hydrocarbon streams that may serve as feed to an aromatic alkylation process. While basic nitrogen compounds are readily removed from hydrocarbon feed stream by even weakly acidic adsorbents, weaker bases, like weakly basic nitrogen compounds are more difficult to remove. Unfortunately, these weakly basic nitrogen compounds are attracted to and poison the catalyst used in aromatics alkylation processes and may cause alkylation catalyst deactivation. Even low concentrations of nitriles in the ranges of parts per million and parts per billion can cumulatively deactivate alkylation catalysts faster than other deactivation mechanisms such as coking. Weak bases typically require strongly acidic materials for their effective removal from a hydrocarbon feed stream. Thus, while clay or resin guard beds are inexpensive means to adsorb basic nitrogen compounds from aromatic alkylation feed streams, more expensive acidic zeolites are typically used to remove weakly basic nitrogen compounds as they have a higher acid site strength and density than other materials, such as acidified clays.

U.S. Pat. No. 6,019,887 teaches using a cationic nonacidic zeolite at no more than 300° C., and U.S. Pat. No. 6,107,535 teaches using silica gel to adsorb nitriles at room temperature from a hydrocarbon stream. U.S. Pat. No. 2,999,861 teaches using an X zeolite to selectively adsorb basic ONCs over weakly basic ONCs including nitriles, nitrates and nitro compounds at −18 to 427° C. U.S. Pat. No. 5,744,686 and U.S. Pat. No. 5,942,650 teach removing water from a benzene stream containing nitriles before removing the nitriles by contacting the benzene stream with nonacidic molecular sieves at −18° to 204° C. U.S. Pat. No. 6,617,482 B1 teaches higher silica zeolites are more effective when water is present. However, only adsorption of NFM in the presence of water is demonstrated at room temperature; adsorption of nitriles is demonstrated only in the absence of water in this reference.

It is desirable, therefore, to provide less expensive means for removing nitrogen compounds, including weakly basic nitrogen compounds, from hydrocarbon feed streams, while effectively removing the nitrogen compounds from the feed stream to prolong the life of more expensive downstream catalysts, such as alkylation catalysts.

SUMMARY OF THE INVENTION

By one aspect, a method for removing weakly basic nitrogen compounds from an aromatic hydrocarbon stream is provided. The method provides a less expensive approach to removing these contaminants from the aromatic hydrocarbon stream than previous techniques.

In accordance with one aspect, the method includes treating a hydrocarbon feed stream including an aromatic compound and a weakly basic nitrogen compound. The method includes contacting the hydrocarbon feed stream with a basic catalyst at contacting conditions including a temperature of at least 50° C. and the presence of water in an amount of at least 50 ppm relative to the hydrocarbon feed stream on a weight basis, to convert the weakly basic nitrogen compound to a basic nitrogen compound to form an intermediate hydrocarbon feed stream and contacting the intermediate stream with an acidic adsorbent to remove the basic nitrogen compound from the hydrocarbon feed stream to produce a treated hydrocarbon stream. More particularly, by one aspect, the hydrocarbon feed stream includes a nitrile and the nitrile is converted to an amine or ammonia when the hydrocarbon feed stream is contacted with the basic catalyst.

By another aspect, a method is provided for producing an alkylated benzene compound. The method includes (i) contacting a hydrocarbon feed stream comprising benzene and a weakly basic nitrogen compound with a basic catalyst to convert the weakly basic nitrogen compound to a basic nitrogen compound; (ii) contacting the hydrocarbon feed stream with an acidic adsorbent to remove the basic nitrogen compound from the hydrocarbon feed stream to produce an alkylation substrate stream and (ii) passing at least a portion of the alkylation substrate stream to an alkylation zone to produce the alkylated benzene compound.

It has been identified that contacting the hydrocarbon feed stream with a basic catalyst at contacting conditions converts weakly basic nitrogen compounds in the feed stream to basic nitrogen compounds allowing the acidic adsorbent to adsorb and remove the basic nitrogen compounds from the feed stream. This produces a treated hydrocarbon feed stream that has a lower concentration of the weakly basic organic nitrogen compounds than the feed stream, and can extend the life of the catalyst in the alkylation zone. Unexpectedly, it has been found that the weakly basic nitrogen compounds may be removed from the stream without the need to contact the feed stream with more expensive acidic zeolites currently used for removing these materials such that less expensive basic catalysts and acidic adsorbents may be used.

DETAILED DESCRIPTION OF THE INVENTION

Methods for treating a hydrocarbon feed stream are provided wherein one or more weakly basic nitrogen compounds are removed from the feed stream by contacting the feed stream with a basic catalyst under contacting conditions to convert the weakly basic nitrogen compounds to basic nitrogen compounds and contacting the feed stream with an acidic adsorbent under contacting conditions to adsorb the basic nitrogen compounds to produce a treated hydrocarbon stream. The treated hydrocarbon stream has a lower weakly basic nitrogen compound content relative to the hydrocarbon feed stream. The hydrocarbon feed stream includes an aromatic compound and a weakly basic nitrogen compound.

The aromatic hydrocarbon compound may be selected from the group consisting of benzene, naphthalene, anthracene, phenanthrene, and substituted derivatives thereof, with benzene and its derivatives being preferred aromatic compounds. The aromatic compound may have one or more of the substituents selected from the group consisting of alkyl groups having from 1 to 20 carbon atoms, hydroxyl groups, and alkoxy groups whose alkyl group also contains from 1 up to 20 carbon atoms. Where the substituent is an alkyl or alkoxy group, a phenyl group can also be substituted on the alkyl chain.

Although unsubstituted and monosubstituted benzenes, naphthalenes, anthracenes, and phenanthrenes are most often used in the practice of this invention, polysubstituted aromatics also may be employed. Examples of suitable alkylatable aromatic compounds in addition to those cited above include biphenyl, toluene, xylene, ethylbenzene, propylbenzene, butylbenzene, pentylbenzene, hexylbenzene, heptylbenzene, octylbenzene, etc.; phenol, cresol, anisole, ethoxy-, propoxy-, butoxy-, pentoxy-, hexoxybenzene, and so forth. Sources of benzene, toluene, xylene, and or other feed aromatics include product streams from naphtha reforming units, aromatic extraction units, recycle streams from styrene monomer production units, and petrochemical complexes for the producing para-xylene and other aromatics. The hydrocarbon feed stream may comprise one or more aromatic hydrocarbon compounds. In an embodiment, the concentration of the aromatic compound in the hydrocarbon feed stream ranges from 5 wt % to 99.9 wt % of the hydrocarbon feed. In another embodiment, the hydrocarbon feed stream comprises between 50 wt % and 99.9 wt % aromatics, and may comprise between 90 wt % and 99.9 wt % aromatics.

The hydrocarbon feed stream weakly basic nitrogen compound may comprise one or more weakly basic ONCs. Weakly basic ONCs may include weakly basic nitriles, such as acetonitrile, propionitrile, and acrylonitrile, and weakly basic amides. The amides may include any amide that can be formed by hydrolysis of the nitriles present in the feed stream.

In an example, the hydrocarbon feed stream has a weakly basic nitrogen component content ranging from 1 ppm-wt to 10 ppm-wt. In another example, the concentration of weakly basic nitrogen compounds in the hydrocarbon feed ranges from 30 ppb-wt (parts per billion by weight) to 1 mole % of the hydrocarbon feed; the concentration of weakly basic nitrogen compounds may range from 100 ppb-wt to 100 ppm-wt of the hydrocarbon feed. In an example, the concentration of weakly basic nitrogen compounds such as nitriles in the hydrocarbon feed ranges from 30 ppb-wt to 100 ppm-wt of the hydrocarbon feed.

By one aspect, the hydrocarbon feed stream is substantially free of unsaturated aliphatic compounds, including unsaturated cyclic hydrocarbons and straight and branched chain olefinic hydrocarbons (olefins) having one or more double bonds. Thus, as used herein the terms "olefins" and "olefinic hydrocarbons" include diolefin compounds. By one aspect the hydrocarbon feed stream is substantially free of an olefin compound, and may be substantially free of a diolefin compound. In an example, the feed is substantially free of unsaturated aliphatic compounds.

Bromine Index is commonly used to assess the unsaturated aliphatic content, including olefins and diolefins, of hydrocarbon mixtures. In an example, the hydrocarbon feed stream has a Bromine Index of below about 500. In another example, the hydrocarbon feed stream has a Bromine Index of below about 100. In one example, the Bromine Index of the hydrocarbon feed stream is less than 5. Herein, the diolefin content of the hydrocarbon streams or mixtures is determined by method UOP980. Unless otherwise noted, the analytical methods used herein such as UOP304 and UOP980 are available from ASTM International, 100 Barr Harbor Drive, West Conshohocken, Pa., USA.

By one aspect, the aromatic compound in the feed stream comprises benzene and the weakly basic nitrogen compound comprises a weakly basic ONC. By another aspect, the aromatic compound comprises benzene and the weakly basic nitrogen compound comprises a nitrile.

In accordance with the method presented herein, the hydrocarbon feed stream is contacted with a basic catalyst under contacting conditions to convert the weakly basic nitrogen compound in the hydrocarbon feed stream to a basic nitrogen compound. By one aspect, the basic catalyst includes a cation-zeolite or cation-inorganic oxide material having a cation (Group 1 and 2 of the Periodic Table) density of at least about 10-mol-% of the framework atoms or total cations made up of inorganic oxides. By another aspect the cation density is at least about 25 mol-%. And by yet another aspect the cation density is at least about 40 mol-%. By one aspect, the basic catalyst may include a basic zeolite or a basic inorganic oxide. By one aspect, the inorganic oxide material is an alumina. Suitable basic zeolites and inorganic oxides may be prepared by adding alkali or alkali earth metals (Group 1 and 2 elements on the Periodic Table) to an inorganic oxide material or a zeolite.

In this regard, the basic catalyst may include a basic zeolite for contacting the hydrocarbon feed stream and removing a nitrogen compound therefrom as is generally known in the art. According to one aspect, the basic zeolite may be in accordance with those generally described in U.S. Pat. No. 5,271,835, which is incorporated by reference herein. The particular zeolite may be selected to have a high cation density of above about 50 in one example, between about 60 and about 99 in another example, and between about 80 and 99 in yet another example. By one aspect, the basic zeolite may include a zeolite having a silicon to aluminum ratio (Si/Al) of between about 1 and about 12. By another aspect, basic zeolite may have a Si/Al ratio of between about 1.2 and 6.0. The basic zeolite according to this aspect may include zeolite LTA, BPH, EMT, Faujasite, LTL, MOR and the mixture of thereof, with at least 50% of framework charges balanced by alkali and/or alkali earth cations.

By one aspect, an inexpensive basic catalyst is used to decrease material costs. In one example, the catalyst includes activated inorganic oxide. In one example, the activated inorganic oxide includes a sodium doped alumina. In another example, the basic catalyst includes sodium X zeolite (Zeolite 13X), which is a relatively inexpensive basic zeolite.

The hydrocarbon feed stream to be treated is contacted with the basic catalyst at contacting conditions to convert the weakly basic nitrogen compound in the feed stream to a basic nitrogen compound. Under contacting conditions, the acidic clay serves as a catalyst to the hydrolysis reaction of converting the weakly basic nitrogen compound in the hydrocarbon feed stream to a basic nitrogen compound. The basic nitrogen compound may then be adsorbed by less expensive acidic adsorbents. In one example, a nitrile in the hydrocarbon feed stream is converted to an amine or ammonia when the feed stream is contacted with the catalyst under contacting conditions. Without intending to be bound by theory, it is believed that contacting a nitrile in the feed stream with the acidic clay at elevated temperatures causes the acidic clay to act as a catalyst to a hydrolysis of the nitrile. Specifically, the hydrolysis of the nitrile in the feed stream converts the nitrile to an amide. Further hydrolysis of the amide in the presence of the basic catalyst and at elevated temperatures converts the amide to an amine and carboxylic acid or ammonia.

The basic catalyst contacting conditions include a temperature of at least 100° C. and is carried out in the presence of water in an amount of at least 50 ppm relative to the hydrocarbon feed stream on a weight basis. Water may be present in an amount equal to or beyond the saturation point of the hydrocarbon feed stream at the basic catalyst contacting conditions contacting conditions. In an example, water is present in an amount of at least 250 ppm relative to the hydrocarbon feed stream on a weight basis. In another embodiment, water is present in an amount ranging from 300 ppm to 800 ppm relative to the hydrocarbon feed stream on a weight basis, and water may be present in an amount ranging from 450 ppm to 700 ppm relative to the hydrocarbon feed stream on a weight basis. The amount of water during contacting may be controlled in any suitable manner. For example, the water content of the hydrocarbon feed may be monitored and controlled by drying and/or adding water or water generating compounds to the feed stream. Water or water generating compounds may be introduced as a separate stream to the contacting step, and the feed stream may be dried to a consistent water level while water or water generating compounds are added to obtain the desired content.

The basic catalyst contacting conditions include a temperature of at least 100° C. and is carried out in the presence of water in an amount of at least 50 ppm relative to the hydrocarbon feed stream on a weight basis. Water may be present in an amount equal to or beyond the saturation point of the intermediate feed stream at the acidic adsorbent contacting conditions. In an example, water is present in an amount of at least 250 ppm relative to the intermediate feed stream on a weight basis. In another embodiment, water is present in an amount ranging from 300 ppm to 800 ppm relative to the intermediate feed stream on a weight basis, and water may be present in an amount ranging from 450 ppm to 700 ppm relative to the intermediate feed stream on a weight basis. The amount of water during contacting may be controlled in any suitable manner. For example, the water content of the intermediate feed may be monitored and controlled by drying and/or adding water or water generating compounds to the feed stream. Water or water generating compounds may be introduced as a separate stream to the contacting step, and the feed stream may be dried to a consistent water level while water or water generating compounds are added to obtain the desired content.

In an example, the basic catalyst contacting temperature ranges from 100° C. to 300° C. and the basic catalyst contacting temperature may range from 125° C. to 300° C. In another example, the basic catalyst contacting temperature ranges from 135° C. to 250° C.; and the basic catalyst contacting temperature may range from 150° C. to 225° C. (please confirm ranges)

Liquid hourly space velocity ("LHSV") through the basic catalyst bed or a basic catalyst zone bed may also be important to the method in order to provide sufficient contact and time of contact between the feed stream and the basic catalyst to facilitate the hydrolysis reaction of the weakly basic nitrogen compound to a basic nitrogen compound. In one example, the LHSV is between about 0.1 and about 10 $hr^{-10}$. In another example, the LHSV is between about 0.2 and about 5 $hr^{-10}$. In yet another example, the LHSV is between about 0.5 and about 2.5 $hr^{-10}$.

By one aspect, the hydrocarbon stream is contacted with an acidic adsorbent to remove the basic nitrogen compound therefrom. More particularly, after the hydrocarbon stream is contacted with the basic catalyst and the weakly basic nitrogen compound is converted to a basic nitrogen compound to form an intermediate stream, the intermediate stream is contacted with an acidic adsorbent to adsorb the basic nitrogen compound from the intermediate stream to form a treated hydrocarbon stream that has a lower concentration of weakly basic nitrogen compounds relative to the hydrocarbon feed stream.

The acidic adsorbent may include an adsorbent material having sufficient acidity to adsorb the basic compounds from the stream. Examples of suitable acidic adsorbents include acidic clays, acidic zeolites, and ion-exchange resins.

By one aspect, the acidic adsorbent includes an acidic zeolite. Suitable acidic zeolites for use in a nitrogen removal zone may include those having a high number of accessible sites that are able to interact with nitrogen containing molecules. Acidic zeolites suitable for removing nitrogen compounds in hydrocarbons includes but not limited to zeolites BPH, EMT, Faujasite, LTL, BEA, MAZ, MOR, MFI, MEI and mixtures thereof. The ranges of silica to alumina ratios depend on the specific structure of the zeolite used, but may typically range from about 2 to about 40. The choice of zeolites depends on the type and concentration of nitrogen compounds and the degree of nitrogen removal desired. In general, at least 50% of framework anion is balanced by proton and preferably at least 70% of the framework anion is balanced by proton.

By another aspect the acidic adsorbent includes an acidic clay. Suitable clays include for example, beidellite, hectorite, laponite, montmorillonite, nontonite, saponite, bentonite, and mixtures thereof. Examples of suitable, commercially available, clay adsorbents include F-Series adsorbents available from BASF and TONSIL adsorbents such as CO 630 G and CO 616 GS available from Sud-Chemie. In an embodiment, the clay adsorbent is an acid activated bentonite and/or montmorillonite clay.

By another aspect, the acidic adsorbent includes ion-exchange resin. Suitable acidic ion-exchange resins include strongly acidic resins, for example those having sulfonic acid groups, like sodium polystyrene sulfonate or polyAMPS, and weakly acidic ion-exchange resins, for example those having carboxylic acid groups.

By one aspect, an inexpensive acidic adsorbent is used, such as acidic clay to reduce material costs.

The hydrocarbon feed stream to be treated is contacted with the acidic adsorbent at contacting conditions to convert the weakly basic nitrogen compound in the feed stream to a basic nitrogen compound. Under contacting conditions, the acidic adsorbent may serve as both a catalyst to further catalyst the conversion of weakly basic nitrogen compounds to basic nitrogen compounds and as an adsorbent to adsorb the basic nitrogen compounds from the stream to remove them from the hydrocarbon feed steam. As mentioned, in one example a nitrile in the hydrocarbon feed stream is converted to an amine or ammonia when the feed stream is contacted with the basic catalyst under contacting conditions. Because the amine or ammonia compound is a much more basic compound than the nitrile, the amine is readily adsorbed by the acid sites on the acidic adsorbent to remove the amine from the hydrocarbon feed stream to produce a treated alkylation substrate stream.

The acidic adsorbent contacting conditions include a temperature of at least 100° C. and is carried out in the presence of water in an amount of at least 50 ppm relative to the hydrocarbon feed stream on a weight basis. Water may be present in an amount equal to or beyond the saturation point of the intermediate feed stream at the acidic adsorbent contacting conditions. In an example, water is present in an amount of at least 250 ppm relative to the intermediate feed stream on a weight basis. In another embodiment, water is present in an amount ranging from 300 ppm to 800 ppm relative to the intermediate feed stream on a weight basis, and water may be present in an amount ranging from 450 ppm to 700 ppm relative to the intermediate feed stream on a weight basis. The amount of water during contacting may be controlled in any suitable manner. For example, the water content of the intermediate feed may be monitored and controlled by drying and/or adding water or water generating compounds to the feed stream. Water or water generating compounds may be introduced as a separate stream to the contacting step, and the feed stream may be dried to a consistent water level while water or water generating compounds are added to obtain the desired content.

In an example, the acidic adsorbent contacting temperature ranges from 100° C. to 300° C. and the acidic adsorbent contacting temperature may range from 125° C. to 300° C. In another example, the acidic adsorbent contacting temperature ranges from 135° C. to 250° C.; and the acidic adsorbent contacting temperature may range from 150° C. to 225° C. (please confirm ranges)

Liquid hourly space velocity ("LHSV") through the acidic adsorbent bed or a an acidic adsorbent zone housing the bed may also be important to the method in order to provide sufficient contact and time of contact between the feed stream and the basic catalyst to facilitate the hydrolysis reaction of the weakly basic nitrogen compound to a basic nitrogen compound. In one example, the LHSV is between about 0.1 and about 10 $hr^{-10}$. In another example, the LHSV is between about 0.2 and about 5 $hr^{-10}$. In yet another example, the LHSV is between about 0.5 and about 2.5 $hr^{-10}$.

By one aspect, the basic catalyst and the acidic adsorbent are held in a nitrogen removal zone. By one aspect, the nitrogen removal zone 30 may include one ore more nitrogen removal vessels or reactors for holding beds of the basic catalyst and the acidic adsorbent. By one aspect, the basic catalyst and the acidic adsorbent are held in different vessels with the basic catalyst vessel positioned upstream of the acidic adsorbent vessel. By another approach, the basic catalyst and the acidic adsorbent beds are housed in the same vessel and may be separated or in a combined single bed configuration. In any event, the hydrocarbon feed stream passes into the nitrogen removal zone. It first contacts the basic catalyst to convert a weakly basic nitrogen compound therein to a basic nitrogen compound. It next contacts the acidic adsorbent to adsorb the basic nitrogen compound.

In one example, at least about 50% of the weakly basic nitrogen compounds are removed from the hydrocarbon feed stream by the methods described herein, as measured, for example by a nitrogen chemiluminescence method, ASTM D4629. In another example, between about 70% and about 99.99% of the weakly basic nitrogen compounds are removed from the hydrocarbon feed stream, and in another example between about 90% and about 99.99% of the weakly basic nitrogen compounds are removed, and in yet another example, between about 95% and about 99.99% of the weakly basic nitrogen compounds are removed.

By another aspect, the method further comprises passing at least a portion of the alkylation substrate stream from the nitrogen removal zone to an alkylation zone wherein the portion of the alkylation substrate stream and an alkylating agent are contacted with an alkylation catalyst to produce an alkylated benzene product. By one aspect, the method includes passing the portion of the alkylation substrate stream from the nitrogen removal zone to the alkylation zone without contacting the alkylation substrate stream with another catalyst or adsorbent material. In this manner, additional expensive catalyst and/or adsorbent materials are not required upstream of the alkylation zone providing savings in materials over previous systems. The alkylation substrate stream may however be passed to a fractionation column or drier before being passed to the alkylation zone in order to remove water or other compounds from the stream.

In the selective alkylation of aromatics alkylation substrate by an olefinic alkylating agent as catalyzed by an acidic catalyst, the olefins may contain from 2 up to at least 20 carbon atoms, and may be branched or linear olefins, either terminal or internal olefins. Thus, the specific nature of the olefin is not particularly important. What the alkylation reactions share in common is that the reactions are conducted under at least partially liquid phase conditions, a criterion readily achieved for the lower members by adjusting reaction pressures. Among the lower olefins, ethylene and propylene are the most important representatives. An olefinic feed stream comprising an alkylating agent may include ethylene and/or propylene. Typically, an olefinic feed stream comprising propylene will be at least 65 wt % pure and an olefinic feed stream comprising ethylene will be over 80 wt % pure. Among the remaining olefins, the class of detergent range olefins consisting of linear olefins containing from 6 up through 20 carbon atoms which have either internal or terminal unsaturation is of particular interest. Linear olefins containing from 8 to 16 carbon atoms and especially those containing from 10 up to 14 carbon atoms are particularly useful as detergent range olefins. Alkylation agents may also be provided by alkyl constituents of a polyalkylbenzene in a transalkylation reaction zone. Diethylbenzene, triethylbenzene and diisopropylbenzene are prominent examples of polyalkylbenzenes that can provide such alkylation agents.

A wide variety of catalysts can be used in the alkylation reaction zone. Suitable catalysts for use in the alkylation zone include catalysts that do not suffer deleterious effects from the presence of water. Preferably, a substantial quantity of water may be tolerated or desired in the presence of the alkylation catalyst. A substantial quantity of water preferably means a water concentration in the reactants entering the alkylation zone of at least 50 wppm. The alkylation reaction zone may have a water content of as little as 20 wppm, to over 200 wppm and up to 1000 wppm or more. The preferred catalyst for use in this invention is a zeolitic catalyst. The catalyst of this invention will usually be used in combination with a refractory inorganic oxide binder. Preferred binders are alumina or silica. Suitable zeolites include zeolite beta described in U.S. Pat. No. 5,723,710, ZSM-5, PSH-3, MCM-22, MCM-36, MCM-49, MCM-56, type Y zeolite, and UZM-8, which includes the aluminosilicate and substituted aluminosilicate zeolites described in U.S. Pat. No. 6,756,030 and the modified UZM-8 zeolites, such as, UZM-8HS which are described in U.S. Pat. No. 7,091,390. Each of U.S. Pat. No. 6,756,030 and U.S. Pat. No. 7,091,390 is herein incorporated by reference in its entirety.

The basic configuration of a catalytic aromatic alkylation zone is known in the art. The feed aromatic alkylation substrate and the feed olefin alkylating agent are preheated and charged to generally from one to four reactors in series. Suitable cooling means may be provided between reactors to compensate for the net exothermic heat of reaction in each of the reactors. Suitable means may be provided upstream of or with each reactor to charge additional feed aromatic, feed olefin, or other streams (e.g., effluent of a reactor, or a stream containing one or more polyalkylbenzenes) to any reactor in the alkylation zone. Each alkylation reactor may contain one or more alkylation catalyst beds. The invention encompasses dual zone aromatic alkylation processes such as those as described in U.S. Pat. No. 7,420,098 which is herein incorporated by reference in its entirety.

The particular conditions under which the alkylation reaction is conducted depends upon the aromatic compound and the olefin used. One necessary condition is that the reaction be conducted under at least partial liquid phase conditions. Therefore, the reaction pressure is adjusted to maintain the olefin at least partially dissolved in the liquid phase. For higher olefins the reaction may be conducted at autogenous pressure. The alkylation conditions usually include a pressure in the range between 1379 kPa(g) and 6985 kPa(g). In an embodiment, the pressure ranges between 2069 kPa(g) and 4137 kPa(g). The alkylation of the aromatic compounds with the olefins in the C2 to C20 range can be carried out at a temperature of 60° C. to 400° C., and preferably from 90° C. to 250° C., for a time sufficient to form the desired product. In a continuous process this time can vary considerably, but is usually from 0.1 to 8 $hr^{-1}$ weight hourly space velocity (WHSV) with respect to the olefin. As used herein, weight hourly space velocity of a component means the weight flow rate of the component per hour divided by the catalyst weight in the same units of measure. In particular, the alkylation of benzene with ethylene can be carried out at temperatures of 150° C. to 250° C. and the alkylation of benzene with propylene at a temperature of 90° C. to 200° C. The ratio of alkylatable aromatic compound to olefin used in the instant process will depend upon the degree of monoalkylation desired as well as the relative costs of the aromatic and olefinic components of the reaction mixture. For alkylation of benzene by propylene, the benzene-to-olefin molar ratio may be as low as 0.1 and as high as 10, with a ratio of 0.5 to 3 being preferred. Where benzene is alkylated with ethylene a benzene-to-olefin ratio may be between 0.1 and 10, with a ratio of 0.5 to 4 being preferred. For detergent range olefins of C6 to C20, a benzene-to-olefin ratio of between 5 and 30 is generally sufficient to obtain the desired monoalkylation yield, with a range between 8 and 20 even more preferred.

The alkylation reaction zone will often provide a wide variety of secondary by-products. For example, in the alkylation of benzene with ethylene to produce ethylbenzene, the reaction zone can also produce di- and triethylbenzene in addition to other ethylene condensation products. Similarly, in the alkylation of benzene with propylene to produce cumene, the reaction zone can produce di- and triisopropylbenzene in addition to still more condensation products. As is well known in the art, these polyalkylated aromatics may contact additional aromatic substrate in a transalkylation zone to produce additional monoalkylated product. See e.g. U.S. Pat. No. 7,622,622 and U.S. Pat. No. 7,268,267. Further, since transalkylation reactions occur in an alkylation reaction zone and alkylation reactions occur in a transalkylation reaction zone, both zones may be referred to as alkylation zones. Thus, as used herein, the term "alkylation zone" encompasses a transalkylation zone. In an embodiment, the alkylated benzene product comprises at least one of ethylbenzene and cumene.

In a further embodiment, the invention is a method for producing an alkylated benzene compound. The method comprises contacting a hydrocarbon feed stream comprising benzene and a weakly basic nitrogen compound with a basic catalyst at contacting conditions. Contacting conditions may comprise a temperature of at least 100° C. and the presence of water in an amount of at least 50 ppm relative to the hydrocarbon feed stream on a weight basis. The basic catalyst contacting step converts the weakly basic nitrogen compound to basic nitrogen compound. The method further comprises contacting the hydrocarbon feed stream with an acidic adsorbent at contacting conditions to remove the basic nitrogen compound from the hydrocarbon feed stream to produce an alkylation substrate stream having a lower concentration of the weakly basic nitrogen compound than the hydrocarbon feed stream. At least a portion of the alkylation substrate stream is passed to an alkylation zone wherein the portion of the alkylation substrate stream and an alkylating agent are contacted with an alkylation catalyst to produce an alkylated benzene compound. By one aspect, the alkylation substrate stream is passed to the alkylation zone after contacting the acidic adsorbent and without being contacted by another catalyst or adsorbent.

The invention claimed is:

1. A method for treating a hydrocarbon feed stream comprising an aromatic compound and a weakly basic nitrogen compound, the method comprising: contacting the hydrocarbon feed stream with a basic catalyst at basic catalyst contacting conditions including a temperature of at least about 50° C. and the presence of water in an amount of at least 50 ppm relative to the hydrocarbon feed stream on a weight basis to convert the weakly basic nitrogen compound to a basic nitrogen compound to form an intermediate stream and contacting the intermediate hydrocarbon stream with an acidic adsorbent at contacting conditions to adsorb the basic nitrogen compound from the intermediate feed stream into the acidic adsorbent to produce a treated hydrocarbon stream lower in concentration of the weakly basic nitrogen compound relative to the hydrocarbon feed stream; wherein the aromatic compound is benzene, the hydrocarbon conversion process includes one of an alkylation and transalkylation process for converting at least a portion of the benzene to ethylbenzene, and the treated hydrocarbon stream is not contacted with any additional catalyst or adsorbent material to remove impurities therefrom before being passed to the alkylation or transalkylation process.

2. The method of claim 1, wherein contacting the hydrocarbon feed stream with a basic catalyst at basic catalyst and contacting the intermediate hydrocarbon stream with an acidic adsorbent are carried out sequentially.

3. The method of claim 1, wherein the basic catalyst and the acidic adsorbent are positioned in a common vessel.

4. The method of claim 1, wherein the basic catalyst and the acidic adsorbent are positioned in different vessels with a basic catalyst vessel positioned upstream of an acidic adsorbent vessel.

5. The method of claim 1, wherein the basic catalyst includes one of basic alumina and a basic zeolite.

6. The method of claim 1, wherein the basic catalyst includes a metal component selected from the group consisting of an alkali metal or an alkali earth metal.

7. The method of claim 1, wherein the basic catalyst has a cation density of above about 25-mol % of framework atoms.

8. The method of claim 1, wherein the acidic adsorbent includes one of acidic clay, an acidic zeolite, and ion-exchange resin.

9. The method of claim 1, wherein the acidic catalyst has a cation density of below about 10 mol-% of framework atoms.

10. The method of claim 1 wherein the basic catalyst contacting conditions include a temperature ranging from about 150° C. to 250° C.

11. The method of claim 1 wherein the hydrocarbon feed stream has a weakly basic nitrogen compound content ranging from 1 ppm-wt to 10 ppm-wt.

12. The method of claim 1 wherein the weakly basic nitrogen compound is an organic nitrogen compound selected from the group consisting of weakly basic organic nitrogen compounds, nitriles, and mixtures thereof.

13. The method of claim 1 wherein the weakly basic nitrogen compound includes nitriles and the basic nitrogen compound includes a compound selected from the group consisting of amines or an ammonia compound.

* * * * *